United States Patent [19]

Gurgiolo

[11] 4,268,684
[45] May 19, 1981

[54] PREPARATION OF CARBAMATES FROM AROMATIC AMINES AND ORGANIC CARBONATES

[75] Inventor: Arthur E. Gurgiolo, Lake Jackson, Tex.

[73] Assignee: The Dow Chemical Company, Midland, Mich.

[21] Appl. No.: 124,200

[22] Filed: Feb. 25, 1980

[51] Int. Cl.$^3$ ............... C07C 125/065; C07C 125/067; C07C 125/073; C07C 125/075
[52] U.S. Cl. ........................................ 560/24; 560/25; 560/26; 560/27; 560/28; 560/29; 560/32; 252/431 C; 252/475; 252/461
[58] Field of Search ...................... 560/24, 25, 26, 27, 560/28, 29, 32

[56] References Cited

U.S. PATENT DOCUMENTS 3,763,217  10/1973  Brill ........................................ 560/24
3,895,054   7/1975  Zajacek et al. ........................ 560/25
3,919,279  11/1975  Rosenthal et al. ............... 260/453 P
3,919,280  11/1975  Rosenthal et al. ............... 260/453 P
3,962,302   6/1975  Rosenthal et al. ............... 260/453 P

OTHER PUBLICATIONS

Mukai et al., Chem. Absts., 87, 5 2961(E), 1977.
Olah, Friedel-Crafts and Related Reactions, vol. 1, Interscience Publishers, pp. 288–291 (1963).

Primary Examiner—Natalie Trousof
Assistant Examiner—G. T. Breitenstein
Attorney, Agent, or Firm—J. G. Carter

[57] ABSTRACT

Carbamates are prepared from organic carbonates and aromatic amines in the presence of zinc, tin or cobalt salts of monovalent organic compounds having a pKa value of less than 2.8 and compounds having more than one carboxyl group per molecule and oxides, sulfides and carbonates at a temperature of at least 200° C.

5 Claims, No Drawings

PREPARATION OF CARBAMATES FROM AROMATIC AMINES AND ORGANIC CARBONATES

BACKGROUND OF THE INVENTION

Lewis acids have been disclosed in U.S. Pat. No. 3,763,217 as being suitable catalysts for reacting an organic carbonate with an aromatic amine to prepare carbamates.

It has been unexpectedly discovered that certain zinc, tin and cobalt salts which are relatively inactive as catalysts for promoting the reaction between organic carbonates and aromatic amines at temperatures of 80°–190° C. are active at temperatures of at least 200° C.

SUMMARY OF THE INVENTION

The present invention pertains to an improvement in a process for preparing a carbamate from an organic carbonate and an aromatic amine in the presence of a catalytic quantity of a Lewis acid under suitable reaction conditions to produce said carbamate wherein the improvement comprises employing as the Lewis acid at least one member selected from the group consisting of (1) zinc or divalent tin or divalent or trivalent cobalt salts of monocarboxylic acids having a pKa value of less than about 2.8;
(2) zinc or divalent tin or divalent or trivalent cobalt salts of organic materials having more than one —COOH group per molecule;
(3) divalent or trivalent cobalt salts of a 1,3 diketone having from about 5 to about 10 carbon atoms, preferably from about 5 to about 6 carbon atoms;
(4) tetravalent alkyl tin compounds or tetravalent alkyl tin oxides represented by the formulas

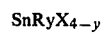

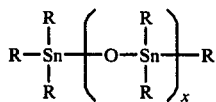

wherein each R is independently a hydrocarbon group having from 1 to about 10, preferably from about 2 to about 4 carbon atoms or a carboxylate group having from 2 to about 10, preferably from 2 to about 4 carbon atoms, X is a halogen atom, preferably chlorine or bromine, x has an average value from 1 to about 5, preferably about 1 and y has a value of 1 to 4;
(5) an inorganic zinc compound selected from zinc carbonate, zinc sulfide and zinc oxide and conducting the reaction at a temperature of at least about 200° C., preferably from about 200° C. to about 300° C.

DETAILED DESCRIPTION OF THE PREFERRED EMBODIMENTS

Suitable organic carbonates which can be employed in the process of the present invention include the alkyl, aryl or alkyl aryl esters of carbonic acid. The ester group can be an alkyl group having up to about 12 carbon atoms, preferably a lower alkyl group containing up to about 6 carbon atoms or the ester group can be an aryl group containing up to about 10 carbon atoms.

Particularly suitable organic carbonates are the cyclic and acyclic organic carbonates such as for example ethylene carbonate, propylene carbonate, styrene carbonate, dimethyl carbonate, diethyl carbonate, dipropyl carbonate, dibutyl carbonate, dihexyl carbonate, methyl ethyl carbonate, methyl butyl carbonate, diphenyl carbonate, methyl phenyl carbonate, mixtures thereof and the like.

Any aromatic amine having a conjugate pKa value of from about 3.5 to about 5.5 is suitable for use herein with those amines having a conjugate pKa value of from about 4 to about 5.4 being preferred.

Suitable such aromatic amines include those represented by the formulas

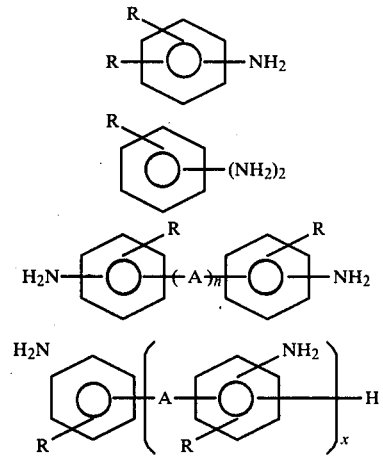

wherein each R is independently hydrogen or a hydrocarbyl or hydrocarbyloxy group containing up to about 8 carbon atoms, preferably up to about 4 carbon atoms, A is a divalent hydrocarbon group having from 1 to about 10 carbon atoms, preferably from 1 to about 6 carbon atoms, n has a value of zero or 1 x has an average value of from about 1.1 to about 10, preferably from about 2 to about 4.

Particularly suitable amines include, for example, aniline, o-, m- or p-toluidine, 2,4-xylidine, 3,4-xylidine, 2,5-xylidine, 4-ethylaniline, 3-propylaniline, 1,3-diaminobenzene, 2,4-diaminotoluene, 2,6-diaminotoluene, 4,4'-diamino-diphenyl methane, 2,4,4'-triamino-diphenyl ether, 2,6-diamino naphthalene, 4,4'-bis-methylene diphenylamine, o-, m- or p-anisidine mixtures thereof and the like.

Suitable zinc or divalent tin or divalent or trivalent cobalt salts of a monocarboxylic acid having a pKa of less than about 2.8 which can be employed as a catalyst herein include, for example, zinc formate, zinc dichloroacetate, zinc trichloroacetate, stannous formate, stannous trichloroacetate, cobaltous formate, cobaltic formate, cobaltous trichloroacetate, cobaltic trichloroacetate, mixtures thereof and the like.

Suitable zinc or divalent tin or divalent or trivalent cobalt salts of organic materials having more than one —COOH group per molecule which can be employed as a catalyst herein include, for example, zinc oxalate, zinc adipate, zinc citrate, zinc terephthalate, zinc polyacrylate, zinc isophthalate, stannous oxalate, stannous adipate, stannous citrate, stannous terephthalate, stannous polyacrylate, stannous isophthalate, cobaltous oxalate, cobaltous adipate, cobaltous citrate, cobaltous terephthalate, cobaltous polyacrylate, cobaltous isophthalate, cobaltic oxalate, cobaltic adipate, cobaltic citrate, cobaltic terephthalate, cobaltic polyacrylate, cobaltic isophthalate, mixtures thereof and the like.

Suitable divalent or trivalent cobalt salts of a 1,3-diketone which can be employed as a catalyst herein include, for example, colbaltous acetylacetonate, cobaltic acetylacetonate, mixtures thereof and the like.

Suitable tetravalent alkyl tin compounds and tetravalent alkyl tin oxides which can be employed as a catalyst herein include, for example, dibutyl stannic dilaurate, dibutyl stannic maleate, triphenyl stannic acetate, tributyl stannic chloride, dibutyl diphenyl tin hexabutyl ditin, tetraphenyl tin, bis(tributyl tin) oxide, tetrabutyl diacetoxy tin oxide dimer, dibutyl tin oxide polymer, butyl tin trihydroxide, tricyclohexyl tin hydroxide, stannic tetrachloride, mixtures thereof and the like.

The reaction is generally conducted at a temperature of at least about 200° C., preferably from about 200° C. to about 300° C. for a time sufficient to complete the reaction depending upon the particular catalyst, reactants and temperature employed. Usually at around 200° C., the time is from about 0.25 hour to about 8 hours, preferably from about 0.5 hour to about 2 hours. The reaction generally should be conducted under conditions at which none of the reactants and/or desired product undergo decomposition.

The quantity of catalyst employed usually depends upon the activity of the particular catalyst. Usually from about 0.001 mole to about 0.2 mole, preferably from about 0.005 mole to about 0.05 mole of catalyst per mole of the reactant present in a stoichiometric quantity is suitable.

The reactants can be employed in an equimolar basis or one may be present in an excess of the other up to about a 20, preferably from about one to about five moles in excess of the other. It is preferred that the organic carbonate reactant be employed in excess of the aromatic amine.

If desirable and/or convenient the reaction can be conducted in the presence of a solvent. Suitable such solvents include, aromatic hydrocarbons, ethers, alcohols such as, for example, benzene, toluene, xylenes, diethyl ether, dioxane, ethanol, propanol, methanol, mixtures thereof and the like.

Uses for the desired carbamate reaction product is suitably discussed by Rosenthal et al in U.S. Pat. Nos. 3,919,279, 3,919,280 and 3,962,302, all of which are incorporated herein by reference.

The following examples are illustrative of the present invention but are not to be construed as to limiting the scope thereof in any manner.

EXAMPLES 1–36 AND COMPARATIVE EXPERIMENTS A–R

In the following examples and comparative experiments, aniline and dimethyl carbonate were premixed employing an excess of the carbonate and a quantity of the mixture was then mixed with catalyst and poured into a stainless steel cylindrical container, 1⅜" internal diameter, and 2¼" internal depth with a wall thickness of 3/16". A stainless steel lid screwed over the reactor with a polytetrafluoroethylene O-ring being used as a seal. Mounted on the lid using stainless steel pipe fittings and parts were a pressure gauge, a pressure relief valve, and a needle valve.

After charging the mixture to the reactor, the lid was sealed by tightening down on the polytetrafluoroethylene O-ring and the reactor was immersed in a hot fluidized sand bath thermostatically controlled at the indicated temperature in the center of the bath. The reactor was heated 10 to 15 minutes then shaken to mix the contents. Then heating was continued for the indicated time. After cooling the contents were analyzed for yields of carbamate and by-products.

The quantity of reactants, catalysts, reaction conditions and results are given in the following Table I.

TABLE I

| EXAMPLE OR EXPT. NO. | CATALYST TYPE | CATALYST g/mole | ANILINE g/mole | DIMETHYL-CARBONATE g/mole | REACTION TIME Hrs. | REACTION TEMP. °C. | CONDITIONS PRESS.[1] psi (kg/cm²) | REACTION PRODUCTS MPC[2] g/mole | NMA[3] g/mole | DPU[4] g/mole | WEIGHT RATIO MPC/NMA | % CONVERSION OF ANILINE TO MPC[5] |
|---|---|---|---|---|---|---|---|---|---|---|---|---|
| A | zinc oxalate | 0.947/0.005 | 5/0.0537 | 25/0.2775 | 4 | 140 | 210 (15) | 0/0 | 0/0 | 0/0 | 0/0 | — |
| 1 | zinc oxalate | 0.47/0.0025 | 5/0.0537 | 25/0.2775 | 2 | 200 | 300 (21) | 4.82/0.032 | 1.57/0.0147 | 0.09/0.0004 | 3.21/1 | 59.4 |
| B | zinc citrate | 0.508/0.00083 | 5/0.0537 | 25/0.2775 | 2 | 140 | 110 (8) | 0.06/0.0004 | 0.44/0.0041 | 0.02/0.0001 | 0.14/1 | 0.75 |
| 2 | zinc citrate | 0.511/0.00084 | 5/0.0537 | 25/0.2775 | 2 | 200 | 350 (25) | 3.34/0.022 | 2.67/0.025 | 0/0 | 1.25/1 | 41.1 |
| C | zinc adipate | 0.524/0.0025 | 5/0.0537 | 25/0.2775 | 2 | 140 | 150 (11) | 0/0 | 0.2/0.0016 | 0/0 | 0/0 | — |
| 3 | zinc adipate | 0.53/0.0025 | 5/0.0537 | 25/0.2775 | 1 | 200 | 220 (15) | 0.77/0.005 | 0.8/0.0075 | 0.44/0.002 | 0.96/1 | 9.5 |
| D | zinc terphthalate | 0.58/0.0025 | 5/0.0537 | 25/0.2775 | 2 | 140 | 160 (11) | 0.03/0.0002 | 0.3/0.0027 | 0/0 | 0.1/1 | 0.37 |
| 4 | zinc terphthalate | 0.58/0.0025 | 5/0.0537 | 25/0.2775 | 2 | 200 | 390 (27) | 3.62/0.024 | 2.38/0.022 | 0.04/0.0002 | 1.52/1 | 44.6 |
| E | zinc (polyacrylic acid) | 5.0/0.0025 | 5/0.0537 | 25/0.2775 | 3.5 | 160 | 200 (14) | 0.06/0.0004 | 0.7/0.0065 | 0.08/0.0004 | 0.09/1 | 0.75 |
| 5 | zinc (polyacrylic acid) | 5.0/0.0025 | 5/0.0537 | 25/0.2775 | 2 | 200 | 600 (42) | 7.07/0.047 | 0.78/0.0073 | 0.06/0.0003 | 9.06/1 | 87.1 |
| F | zinc salt of DOWEX® CCR-2 | 2.66[6]/0.04 | 5/0.0537 | 25/0.2775 | 4 | 140 | 200 (14) | 0/0 | 0/0 | 0/0 | 0/0 | — |
| G | zinc salt of DOWEX® CCR-2 | 2.66[6]/0.04 | 5/0.0537 | 25/0.2775 | 3 or more | 160 | 240 (17) | 0/0 | 0/0 | 0/0 | 0/0 | — |
| 6 | zinc salt of DOWEX® CCR-2 | 2.66[6]/0.04 | 5/0.0537 | 25/0.2775 | 2 | 200 | 390 (27) | 2.12/0.014 | 2.88/0.003 | 0.012/0.0001 | 0.74/1 | 26.1 |
| H | zinc isophthalate | 0.580/0.0025 | 5/0.0537 | 25/0.2775 | 2 | 140 | 160 (11) | 0.13/0.0009 | 0.32/0.003 | 0.02/0.0001 | 0.4/1 | 1.7 |
| 7 | zinc isophthalate | 0.580/0.0025 | 5/0.0537 | 25/0.2775 | 7 | 200 | 750 (53) | 4.4/0.029 | 1.1/0.010 | 0.07/0.0003 | 4/1 | 54 |
| I | zinc itaconate | 0.484/0.0025 | 5/0.0537 | 25/0.2775 | 2 | 140 | 150 (11) | 2.3/0.015 | 1.14/0.011 | 0.16/0.0008 | 2/1 | 27.9 |
| 8 | zinc itaconate | 0.484/0.0025 | 5/0.0537 | 25/0.2775 | 4 | 200 | 350 (25) | 0.5/0.0033 | 0.65/0.006 | 0.14/0.0007 | 0.8/1 | 6.1 |
| J | zinc trichloroacetate | 0.97/0.0025 | 5/0.0537 | 25/0.2775 | 2 | 140 | 150 (11) | 0.3/0.002 | 0.42/0.004 | 0.1/0.0004 | 0.7/1 | 3.7 |
| 9 | zinc trichloroacetate | 0.97/0.0025 | 5/0.0537 | 25/0.2775 | 1 | 200 | 460 (32) | 1.4/0.0093 | 0.32/0.003 | 0.04/0.0002 | 4.4/1 | 17.3 |
| 10 | zinc carbonate | 1.57/0.0125 | 5/0.0537 | 25/0.2775 | 2 | 200 | 350 (25) | 7.8/0.052 | 0.34/0.0032 | 0.05/0.00022 | 23/1 | 96 |
| 11 | zinc carbonate | 0.314/0.0025 | 5/0.0537 | 25/0.2775 | 2 | 200 | 360 (25) | 7.5/0.05 | 0.23/0.0022 | 0.05/0.00022 | 32.6/1 | 92.4 |
| 12 | zinc oxide | 0.407/0.005 | 5/0.0537 | 25/0.2775 | 2 | 200 | 390 (27) | 3.03/0.02 | 2.8/0.026 | 0.07/0.0003 | 1.1/1 | 37.3 |
| 13 | zinc sulfide | 1.0/0.01 | 5/0.0537 | 25/0.2775 | 2 | 200 | 390 (27) | 3.4/0.0224 | 2.6/0.024 | 0.04/0.00017 | 1.3/1 | 41.8 |
| K | zinc carbonate | 0.314/0.0025 | 5/0.0537 | 25/0.2775 | 0.5 | 180 | 115 (8) | 0.35/0.0023 | 0.26/0.0024 | 0.14/0.0007 | 1.4/1 | 4.3 |
| L | zinc carbonate | 0.314/0.0025 | 5/0.0537 | 25/0.2775 | 0.5 | 190 | 190 (13) | 0.33/0.0022 | 0.55/0.005 | 0.14/0.0007 | 0.6/1 | 4.1 |
| 14 | zinc carbonate | 0.314/0.0025 | 5/0.0537 | 25/0.2775 | 0.5 | 200 | 250 (18) | 5.24/0.035 | 0.55/0.005 | 0.13/0.0006 | 9.5/1 | 64.6 |
| 15 | zinc carbonate | 1.567/0.0125 | 5/0.0537 | 25/0.2775 | 0.25 | 250 | 600 (42) | 7.62/0.0504 | 0.28/0.0026 | 0.033/0.00016 | 27.2/1 | 93.9 |
| 16 | zinc carbonate | 1.567/0.0125 | 3.05/0.057[7] | 22.52/0.25 | 0.5 | 250 | 750 (53) | 8.1/0.0348[8] | 0/0 | 0/0 | 0/0 | 68[8] |
| M | dibutyl tin dilaurate | 1.58/0.0025 | 5/0.0537 | 25/0.2775 | 1 | 140 | 120 (8) | 0.31/0.002 | 0.17/0.0016 | 0.13/0.0006 | 1.26/1 | 3.8 |
| 17 | dibutyl tin dilaurate | 1.58/0.0025 | 5/0.0537 | 25/0.2775 | 1 | 200 | 240 (17) | 7.1/0.047 | 0.16/0.0015 | 0.13/0.0006 | 44.4/1 | 87.5 |
| N | tetrabutyl diacetoxy tin oxide dimer | 3.0/0.005 | 5/0.0537 | 25/0.2775 | 2.5 | 140 | 150 (11) | 3.6/0.024 | 0.18/0.0017 | 0.28/0.013 | 20/1 | 44.2 |
| 18 | tetrabutyl diacetoxy tin oxide dimer | 0.75/0.00125 | 5/0.0537 | 25/0.2775 | 1 | 200 | 210 (15) | 7.41/0.049 | 0.33/0.0031 | 0.13/0.0006 | 22.5/1 | 91.3 |
| 19 | bis(tributyl tin) oxide | 0.75/0.0025 | 5/0.0537 | 25/0.2775 | 1 | 200 | 210 (15) | 0.84/0.0056 | 0.7/0.0065 | 0.12/0.00056 | 1.2/1 | 10.4 |
| 20 | triphenyl tin acetate | 1.023/0.0025 | 5/0.0537 | 25/0.2775 | 1 | 200 | 240 (17) | 4.16/0.0275 | 0.51/0.0048 | 0.13/0.0006 | 8.16/1 | 51.3 |
| 21 | dibutyl tin oxide polymer | 0.622/0.0025 | 5/0.0537 | 25/0.2775 | 1 | 200 | 220 (15) | 7.11/0.047 | 0.17/0.0016 | 0.06/0.0003 | 41.8/1 | 87.6 |
| 22 | dibutyl tin maleate | 0.873/0.0025 | 5/0.0537 | 25/0.2775 | 1 | 200 | 280 (20) | 5.27/0.035 | 0.23/0.0022 | 0.16/0.00075 | 22.9/1 | 65.0 |
| 23 | tributyl tin chloride | 0.814/0.0025 | 5/0.0537 | 25/0.2775 | 1 | 200 | 300 (21) | 0.90/0.006 | 1.25/0.012 | 0.23/0.001 | 0.72/1 | 10.8 |
| 24 | dibutyl diphenyl tin | 0.97/0.0025 | 5/0.0537 | 25/0.2775 | 4 | 200 | 310 (22) | 0.05/0.0003 | 0.75/0.007 | 0.16/0.00075 | 0.07/1 | 0.6 |
| 25 | hexabutyl ditin | 0.725/0.0025 | 5/0.0537 | 25/0.2775 | 1 | 200 | 310 (22) | 0.47/0.0031 | 0.72/0.0067 | 0.17/0.0008 | 0.7/1 | 6 |
| 26 | tetraphenyl tin | 1.068/0.0025 | 5/0.0537 | 25/0.2775 | 1 | 200 | 310 (22) | 2.82/0.0187 | 0.7/0.0063 | 0.14/0.0007 | 4.2/1 | 34.7 |
| 27 | butyl tin trihydroxide | 0.567/0.0025 | 5/0.0537 | 25/0.2775 | 1 | 200 | 300 (21) | 6.15/0.041 | 0.37/0.0034 | 0.10/0.0005 | 16.6/1 | 75.6 |
| 28 | tricyclohexyl tin hydroxide | 0.525/0.0025 | 5/0.0537 | 25/0.2775 | 1 | 200 | 280 (20) | 0.71/0.0047 | 0.76/0.0071 | 0.18/0.0008 | 0.9/1 | 9 |
| 29 | dibutyl tin oxide polymer | 0.50/0.002 | 3.05/0.057[7] | 27.52/0.306 | 1 | 250 | 525 (37) | 1.3/0.005[8] | 0/0 | 0/0 | 0/0 | 10[8] |
| 30 | cobaltous naphthenate (6% Co) | 2.455/0.0025 | 5/0.0537 | 25/0.2775 | 2 | 200 | 290 (20) | 7.0/0.046 | 0.36/0.0034 | 0.05/0.0025 | 19.4/1 | 86 |
| 31 | cobaltous carbonate | 2.0/0.0168 | 5/0.0537 | 25/0.2775 | 1 | 200 | 320 (22) | 1.51/0.01 | 1.16/0.01 | 0.14/0.0007 | 1.3/1 | 18.6 |

TABLE I-continued

| EXAMPLE OR EXPT. NO. | CATALYST TYPE | CATALYST g/mole | ANILINE g/mole | DIMETHYL CARBONATE g/mole | REACTION CONDITIONS TIME Hrs. | REACTION CONDITIONS TEMP. °C. | CONDITIONS PRESS.[1] psi (kg/cm²) | REACTION PRODUCTS MPC[2] g/mole | REACTION PRODUCTS NMA[3] g/mole | REACTION PRODUCTS DPU[4] g/mole | WEIGHT RATIO MPC/NMA | % CONVERSION OF ANILINE TO MPC[5] |
|---|---|---|---|---|---|---|---|---|---|---|---|---|
| 32 | cobaltous naphthenate (6% Co) | 0.5/0.0005 | 5/0.0537 | 25/0.2775 | 0.5 | 250 | 750 (53) | 4.44/0.0294 | 1.5/0.014 | 0.96/0.0045 | 3/1 | 54.7 |
| O | cobaltous naphthenate (6% Co) | 2.455/0.0025 | 5/0.0537 | 5/0.0537 | 1 | 140 | 120 (8) | 0.18/0.001 | 0.09/0.0008 | 0/0 | 0.2/1 | 1.8 |
| 33 | cobaltous naphthenate (6% Co) | 4.9/0.005 | 3.05/0.05[7] | 22.52/0.25 | 1 | 250 | 750 (53) | 7.08/0.038[8] | 0/0 | 0/0 | 0/0 | 59.2[8] |
| 34 | cobaltous acetylacetonate | 0.643/0.0025 | 5/0.0537 | 25/0.2775 | 2 | 200 | 200 (14) | 5.95/0.0393 | 0.75/0.007 | 0.03/0.00013 | 7.93/1 | 73.2 |
| 35 | cobaltic acetylacetonate | 0.891/0.0025 | 5/0.0537 | 25/0.2775 | 2 | 200 | 200 (14) | 5.48/0.363 | 0.87/0.008 | 0.125/0.0006 | 6.3/1 | 67.5 |
| 36 | cobaltous acetate .4 H₂O | 0.623/0.0025 | 5/0.0537 | 25/0.2775 | 1 | 200 | 220 (15) | 3.25/0.022 | 0.97/0.009 | 0.174/0.0008 | 3.4/1 | 40.0 |
| P | antimony trichloride | 0.57/0.0025 | 5/0.0537 | 25/0.2775 | 2 | 200 | 280 (20) | 1.7/0.011 | 0.85/0.008 | 0.06/0.00026 | 2/1 | 21.2 |
| Q | uranium trioxide | 1.602/0.0056 | 18.6/0.2 | 18/0.2 | 2 | 200 | 700 (49) | 4.464/0.0295 | 6.37/0.06 | 0.67/0.003 | 0.7/1 | 14.8 |
| R | uranium dioxide | 1.512/0.0056 | 18.6/0.2 | 18/0.2 | 2 | 200 | 650 (46) | 4.544/0.0301 | 6.35/0.06 | 0.64/0.003 | 0.72/1 | 15.0 |

[1]Pressure indicated is gauge pressure.
[2]MPC is methyl phenyl carbamate.
[3]NMA is N-methyl aniline.
[4]DPU is diphenyl urea
[5]Calculated by dividing moles of MPC by moles of aniline employed and multiplying by 100.
[6]20 grams of a weak acid cation exchange resin containing carboxylic acid groups within a styrene divinyl benzene matrix having an exchange capacity of 4.1 meq/ml of wet resin converted to the zinc salt and containing 13.3% zinc. The ion exchange resin prior to converting to the zinc salt by contacting with a 4% aqueous solution of zinc sulfate is available from The Dow Chemical Company as DOWEX® CCR-2.
[7]The amine was 2,4-toluene diamine instead of aniline.
[8]2,4-toluene diamine dicarbamate instead of MPC.

I claim:

1. In a process for preparing carbamates from an organic carbonate and an aromatic amine in the presence of catalytic quantities of a catalyst; the improvement which comprises employing as the catalyst at least one member selected from the group consisting of
   (1) zinc or divalent tin salts of monocarboxylic acids having a pKa value of less than 2.8 other than such salts of trifluoroacetic acid;
   (2) divalent cobalt or trivalent cobalt salts of monocarboxylic acids having a pKa value of less than about 2.8;
   (3) zinc or divalent tin or divalent cobalt or trivalent cobalt salts of organic materials having more than one —COOH group per molecule;
   (4) divalent cobalt or trivalent cobalt salts of a 1,3 diketone having from about 5 to about 10 carbon atoms;
   (5) tetravalent alkyl tin compounds or tetravalent alkyl tin oxides represented by the formulas

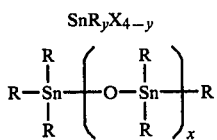

wherein each R is independently a hydrocarbon group having from 1 to about 10, or a carboxylate group having from 2 to about 10, X is a halogen atom, x has an average value from 1 to about 5, and y has a value of 1 to 4; and
   (6) an inorganic zinc compound selected from zinc carbonate, zinc sulfide and zinc oxide and conducting the reaction at a temperature of at least about 200° C.

2. The process of claim 1 wherein the reaction temperature is from about 200° C. to about 300° C.

3. The process of claims 1 or 2 wherein said catalyst is zinc carbonate, the zinc salt of an acid containing ion exchange resin, zinc salt of polyacrylic acid, cobaltous acetylacetonate, or mixtures thereof.

4. The process of claim 1 or 2 wherein said aromatic amine is aniline, 2,4-toluene diamine, 2,6-toluene diamine, methylene dianiline or mixtures thereof and said organic carbonate is dimethylcarbonate, diethylcarbonate, diphenylcarbonate, ethylene carbonate, propylene carbonate or mixtures thereof.

5. The process of claim 3 wherein said aromatic amine is aniline, 2,4-toluene diamine, 2,6-toluene diamine, methylene dianiline or mixtures thereof and said organic carbonate is dimethylcarbonate, diethylcarbonate, diphenylcarbonate, ethylene carbonate, propylene carbonate or mixtures thereof.

* * * * *